(12) United States Patent
Wiggins et al.

(10) Patent No.: US 9,075,024 B1
(45) Date of Patent: *Jul. 7, 2015

(54) METHODS FOR DETERMINING WEAR VOLUME OF A TESTED POLYCRYSTALLINE DIAMOND ELEMENT

(71) Applicant: US SYNTHETIC CORPORATION, Orem, UT (US)

(72) Inventors: Jason K. Wiggins, Draper, UT (US); Richard B. Smith, Spring, TX (US); Bryan H. Jansen, Provo, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/273,409

(22) Filed: May 8, 2014

Related U.S. Application Data

(63) Continuation of application No. 13/559,711, filed on Jul. 27, 2012, now Pat. No. 8,760,668.

(60) Provisional application No. 61/514,548, filed on Aug. 3, 2011.

(51) Int. Cl.
*G01B 11/12* (2006.01)
*G01N 21/84* (2006.01)
*G01N 19/00* (2006.01)

(52) U.S. Cl.
CPC ............... *G01N 21/84* (2013.01); *G01N 19/00* (2013.01); *G01N 2021/8477* (2013.01)

(58) Field of Classification Search
CPC ... E21B 17/1085; E21B 41/00; E21B 17/042; E21B 7/046; E21B 10/60; E21B 21/103; E21B 29/00; E21B 33/06; E21B 33/063; E21B 43/11; E21B 7/12; E21B 7/14; E21B 7/15; E21B 19/004
See application file for complete search history.

(56) References Cited

U.S. PATENT DOCUMENTS

| | | | |
|---|---|---|---|
| 4,268,276 A | 5/1981 | Bovenkerk |
| 4,410,054 A | 10/1983 | Nagel et al. |
| 4,468,138 A | 8/1984 | Nagel |
| 4,560,014 A | 12/1985 | Geczy |
| 4,738,322 A | 4/1988 | Hall et al. |
| 4,811,801 A | 3/1989 | Salesky et al. |
| 4,913,247 A | 4/1990 | Jones |
| 5,016,718 A | 5/1991 | Tandberg |
| 5,021,675 A | 6/1991 | Fischer |
| 5,092,687 A | 3/1992 | Hall |

(Continued)

OTHER PUBLICATIONS

U.S. Appl. No. 11/545,929, filed Oct. 10, 2006, Bertagnolli et al.

(Continued)

*Primary Examiner* — Michael P Stafira
(74) *Attorney, Agent, or Firm* — Dorsey & Whitney LLP

(57) ABSTRACT

Embodiments of methods are disclosed for characterizing a tested polycrystalline diamond ("PCD") element, such as a PDC cutting element. In an embodiment, a method for characterizing a tested PCD element is disclosed. An initial volume of a PCD element is measured using a coordinate measuring machine ("CMM"). A workpiece is cut with the PCD element so that the PCD element develops a wear flat. A post-cut volume of the PCD element is measured after cutting the workpiece using the CMM. A wear volume of the PCD element is determined at least partially based on the post-cut volume and the initial volume of the PCD element.

28 Claims, 8 Drawing Sheets

(56) References Cited

U.S. PATENT DOCUMENTS

| | | |
|---|---|---|
| 5,120,327 A | 6/1992 | Dennis |
| 5,135,061 A | 8/1992 | Newton, Jr. |
| 5,154,245 A | 10/1992 | Waldenstrom et al. |
| 5,180,022 A | 1/1993 | Brady |
| 5,364,192 A | 11/1994 | Damm et al. |
| 5,368,398 A | 11/1994 | Damm et al. |
| 5,460,233 A | 10/1995 | Meany et al. |
| 5,480,233 A | 1/1996 | Cunningham |
| 5,544,713 A | 8/1996 | Dennis |
| 5,871,391 A | 2/1999 | Pryor |
| 5,930,143 A | 7/1999 | Savazzi |
| 6,633,379 B2 | 10/2003 | Roesner et al. |
| 6,793,681 B1 | 9/2004 | Pope et al. |
| 7,495,759 B1 | 2/2009 | Cheng et al. |
| 7,514,680 B1 | 4/2009 | Kley |
| 7,866,418 B2 | 1/2011 | Bertagnolli et al. |
| 7,870,913 B1 | 1/2011 | Sexton et al. |
| 2002/0186370 A1 | 12/2002 | Roesner et al. |
| 2005/0050942 A1 | 3/2005 | Schmitt |
| 2009/0133468 A1 | 5/2009 | Biskeborn |
| 2011/0037983 A1 | 2/2011 | Davies |

OTHER PUBLICATIONS

U.S. Appl. No. 61/514,548, filed Aug. 3, 2011, Wiggins et al.
U.S. Appl. No. 12/961,787, filed Dec. 7, 2010, Mukhopadhyay et al.
U.S. Appl. No. 13/559,711, filed Jul. 27, 2012, Wiggins et al.
U.S. Appl. No. 13/559,711, Oct. 29, 2013, Notice of Allowance.
U.S. Appl. No. 13/559,711, Feb. 10, 2014, Notice of Allowance.
U.S. Appl. No. 13/559,711, Jun. 4, 2014, Issue Notificiation.

METHODS FOR DETERMINING WEAR VOLUME OF A TESTED POLYCRYSTALLINE DIAMOND ELEMENT

CROSS-REFERENCE TO RELATED APPLICATIONS

This application is a continuation of U.S. application Ser. No. 13/559,711 filed on 27 Jul. 2012, which claims priority to U.S. Provisional Application No. 61/514,548 filed on 3 Aug. 2011, the disclosure of each of the foregoing applications is incorporated herein, in its entirety, by this reference.

BACKGROUND

Wear-resistant, superabrasive compacts are utilized in a variety of mechanical applications. For example, polycrystalline diamond compacts ("PDCs") are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller cone drill bits and fixed cutter drill bits. A PDC cutting element typically includes a superabrasive diamond layer (also known as a diamond table). The diamond table is formed and bonded to a substrate using an ultra-high pressure, ultra-high temperature ("HPHT") process. The substrate is often brazed or otherwise joined to an attachment member, such as a stud or a cylindrical backing. The substrate is typically made of tungsten or tungsten carbide.

A rotary drill bit typically includes a number of PDC cutting elements affixed to a drill bit body. A stud carrying the PDC may be used as a PDC cutting element when mounted to a bit body of a rotary drill bit by press-fitting, brazing, or otherwise securing the stud into a receptacle formed in the bit body. The PDC cutting element may also be brazed directly into a preformed pocket, socket, or other receptacle formed in the bit body.

Conventional PDCs are normally fabricated by placing a cemented carbide substrate into a container or cartridge with a volume of diamond particles positioned on a surface of the cemented carbide substrate. A number of such cartridges may be loaded into an HPHT press. The substrates and volume of diamond particles are then processed under HPHT conditions in the presence of a catalyst material that causes the diamond particles to bond to one another to form a matrix of bonded diamond grains (i.e., crystals) defining a polycrystalline diamond ("PCD") table. The catalyst material is often a metal-solvent catalyst, such as cobalt, nickel, iron, or alloys thereof that is used for promoting intergrowth of the diamond particles.

In one conventional approach, a constituent of the cemented carbide substrate, such as cobalt from a cobalt-cemented tungsten carbide substrate, liquefies and sweeps from a region adjacent to the volume of diamond particles into interstitial regions between the diamond particles during the HPHT process. The cobalt acts as a catalyst to promote intergrowth between the diamond particles, which results in formation of bonded diamond grains. During the HPHT process other components of the cemented carbide substrate, such as tungsten and carbon, may also migrate into the interstitial regions between the diamond crystals. The diamond crystals become mutually bonded to form a matrix of PCD, with interstitial regions between the bonded diamond grains being occupied by the solvent catalyst.

The wear resistance and thermal stability are important performance characteristics of a PDC and can vary greatly depending on the composition, structure, and manufacturing process used to fabricate the PDC. Therefore, it is important to be able to accurately characterize PDCs that are tested in order to be able to better design and manufacture PDCs.

SUMMARY

Embodiments of methods are disclosed for characterizing a tested PCD element (e.g., a PDC cutting element) and designing PCD elements. In an embodiment, a method for characterizing a PCD element that is tested is disclosed. An initial volume of a PCD element is measured using a coordinate measuring machine ("CMM"). A workpiece is cut with the PCD element so that the PCD element develops a wear volume. A post-cut volume of the PCD element is measured after cutting the workpiece using the CMM. A wear volume of the PCD element is determined at least partially based on the post-cut volume and the initial volume.

In an embodiment, a method for designing a manufacturing process for a PCD element is disclosed. An initial volume of the PCD element is determined using a CMM prior to cutting a workpiece with a PCD element. A workpiece is cut with the PCD element so that the PCD element develops a wear flat. A post-cut volume of the PCD element is measured after cutting using the CMM. A volume of the wear flat is determined at least partially based on the post-cut volume and the initial volume of the PCD element. A manufacturing process used to fabricate the PCD element is adjusted at least partially based on the volume of the wear flat.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

I. Embodiments of Methods for Characterizing and Designing PDCs

Figure 1:
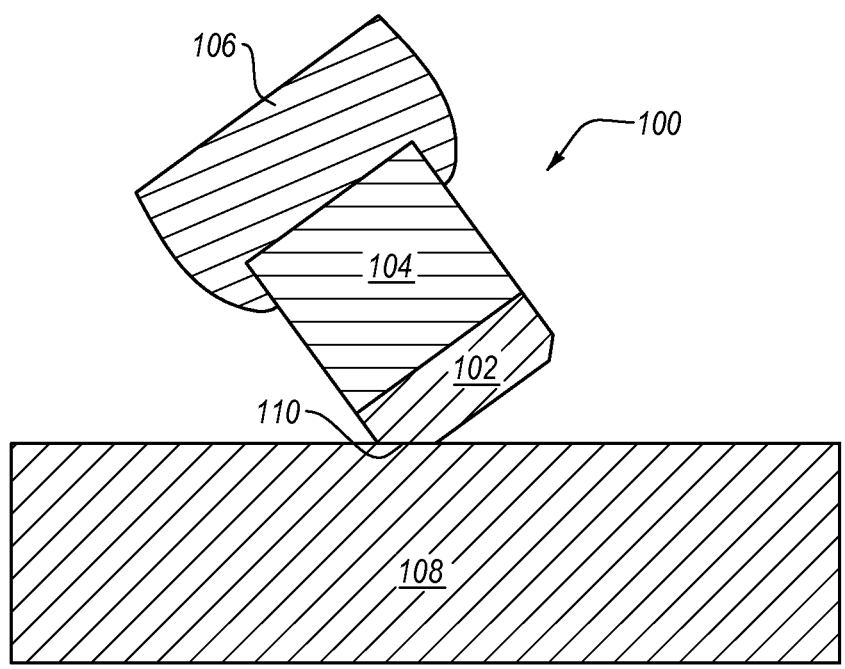
FIG. 1 is a cross-sectional view of a PCD element being tested in a vertical turret lathe test fixture as the PCD element cuts a workpiece and develops a wear flat to be measured.
Figure 2:
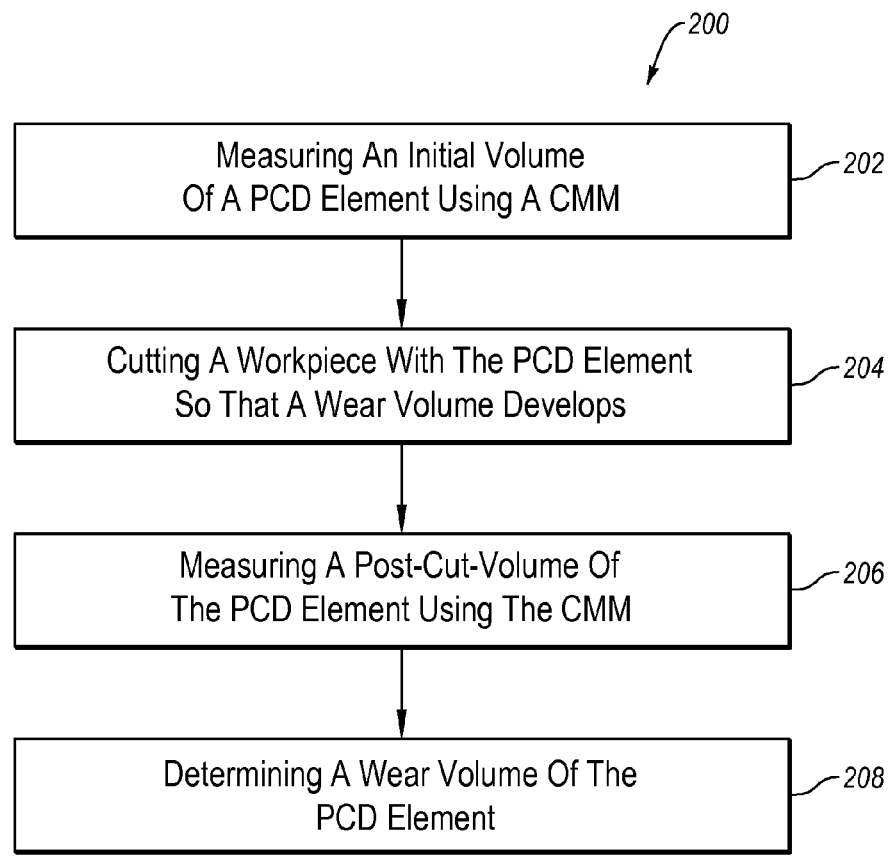
FIG. 2 is a flow chart of a method of determining a wear volume of a PCD element according to an embodiment.

Embodiments of the invention are directed to methods for determining a wear volume of a PCD element (e.g., a PDC or freestanding PCD element) that is tested on a workpiece and characterized using a CMM. FIG. 1 is a cross-sectional view of a PCD element 100 (depicted as a PDC having a PCD table 102 bonded to a substrate 104) being tested in a vertical turret lathe test fixture 106 as the PCD element/PDC 100 cuts a workpiece 108 and develops a wear volume 110 due to material from the PCD element 100 wearing away. A wear volume is also sometimes referred to as a "wear flat" by those of ordinary skill in the art. FIG. 2 is a flow chart of a method 200 of determining a wear volume of a PCD element that is tested on a workpiece according to an embodiment. The PCD element that is tested may be any of the PCD elements disclosed herein, such as a PDC or a freestanding PCD element/table. When the PCD element is being tested, the wear volume to be determined may be only in the PCD table or may further extend into the substrate to which it is attached.

The method 200 includes an act 202 of measuring an initial volume of a PCD element using a CMM. Next, the method 200 includes an act 204 of cutting a workpiece with the PCD element so that a wear flat develops. After developing the wear volume, in act 206, a post-cut volume of the PCD element may be measured using the CMM. In act 208, a wear volume of the PCD element may be determined. The wear volume is the volume of the PCD element that was removed during cutting of the workpiece. For example, the volume of the wear volume may be determined by calculating the difference between the initial volume of the PCD element and the post-cut volume of the PCD element.

The CMM may be configured as a contact or a non-contact CMM. In an embodiment, the CMM may be a laser CMM that measures volume of the PCD element by scanning the PCD element with a laser. The laser CMM is configured to scan the PCD element with a laser and generate a plurality of points (i.e., a point cloud) from the received reflected laser light from which an accurate computer-generated model can be generated. One suitable laser CMM is the Smartscope Lazer commercially available from Optical Gaging Products, Inc. of Rochester, N.Y. In other embodiments, the CMM may be a mechanical contact-type CMM that uses a stylus tip to contact the PCD element being measured to generate the computer model thereof. In other embodiments, the CMM may be a non-laser optical CMM, such as a CMM that uses a white light source. Use of a CMM to measure the volume of the PCD element provides a highly accurate and repeatable technique, particularly in comparison to an optical or electron microscope.

Figure 3:
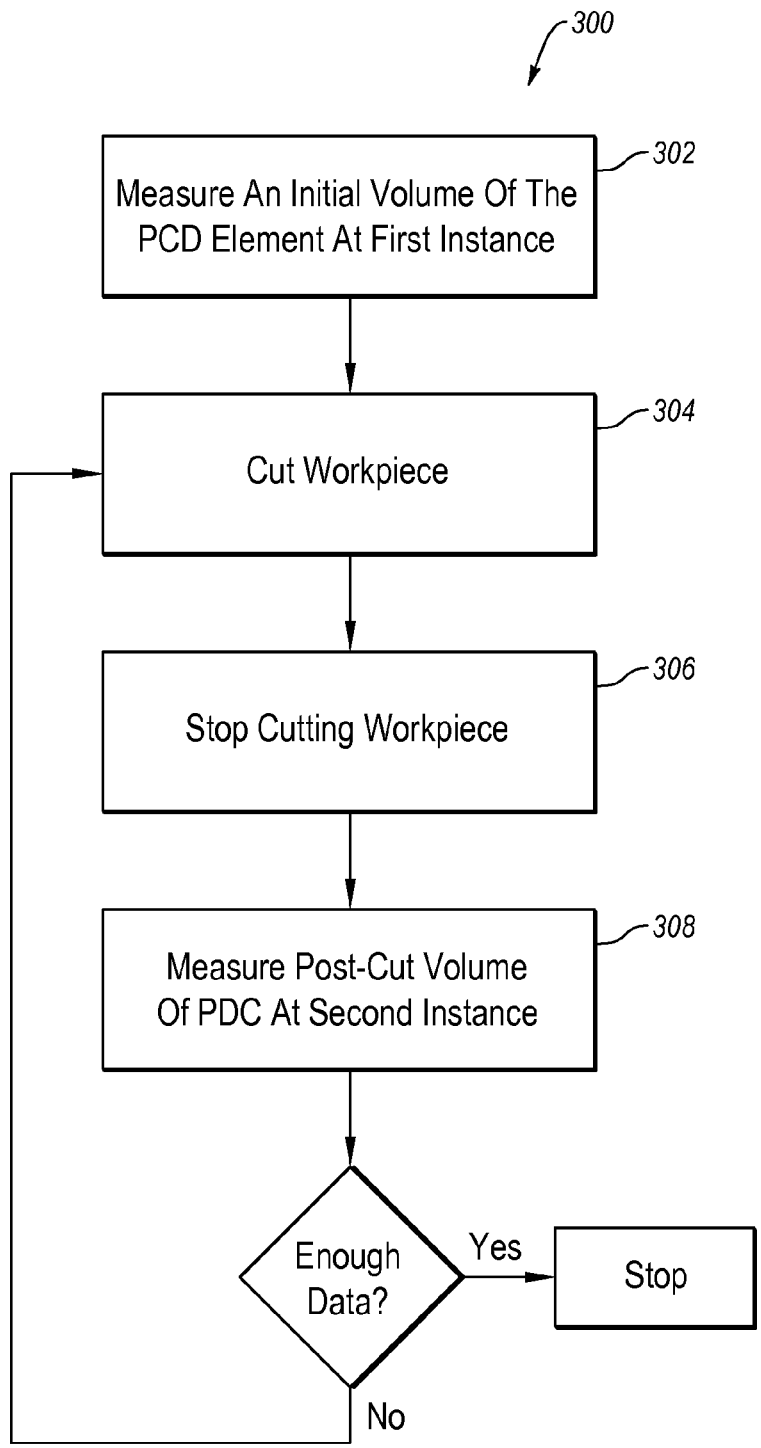
FIG. 3 is a flow chart of a method of determining a volume of a PCD element at different stages during cutting a workpiece so that a $G_{ratio}$ graph can be determined according to an embodiment.

FIG. 3 is a flow chart of a method 300 of determining the volume of a PCD element at different stages during cutting a workpiece so that a $G_{ratio}$ graph can be determined according to an embodiment. The method 300 includes an act 302 of measuring an initial volume of the PCD element at a first instance using a CMM, which may be an initial unworn volume of the PCD element or an initial wear volume due to the PCD element having already been used to cut a workpiece. Next, in act 304, the PCD element is used to cut the workpiece. In act 306, the cutting process is stopped and, in act 308, a subsequent volume of the PCD element is measured at a second instance. In an embodiment, wear volume data may be computed to generate a $G_{ratio}$ graph, and the test is stopped. If more wear volume data is desired, the process of cutting the workpiece at act 304 with the PCD element and measuring the volume of the PCD element is repeated until a sufficient amount of volume data is generated.

Figure 4:
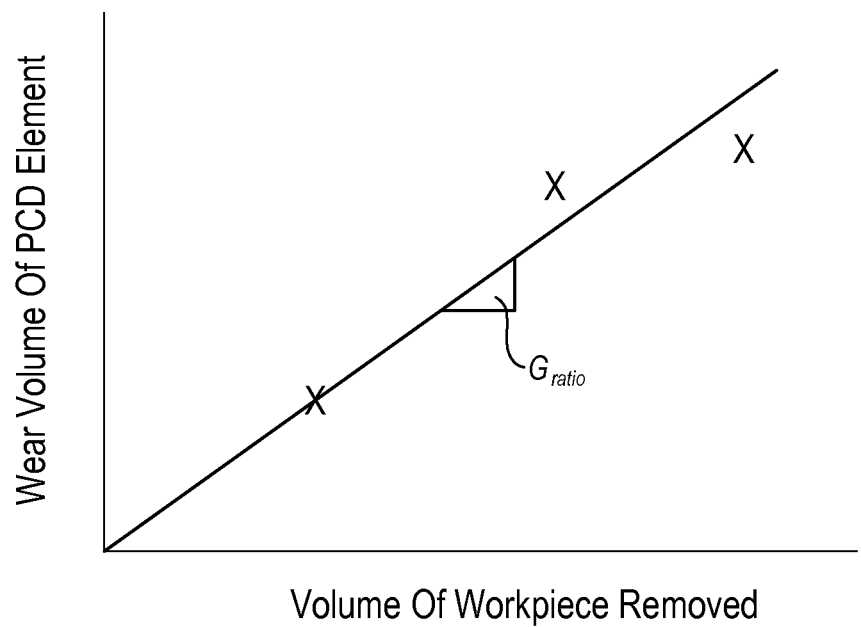
FIG. 4 is a graph of wear volume of a PCD element versus volume of workpiece removed by the PCD element during a vertical turret lathe test so that a $G_{ratio}$ can be determined.

FIG. 4 is a $G_{ratio}$ graph of a hypothetical PCD element tested in a vertical turret lathe. Typically, a generally linear graph of wear volume of the PCD element to volume of workpiece removed by the PCD element is generated. A relatively lower slope of $G_{ratio}$ is indicative of higher wear resistance for the PCD element.

Non-limiting examples of specific cutting tests that may be performed on the PCD elements to be tested using a vertical turret lathe are discussed below. For example, abrasion resistance of a PCD element may be evaluated by measuring the volume of the PCD element removed versus the volume of a Barre granite workpiece removed, while the workpiece is cooled with water. The test parameters may include a depth of cut for the PCD element of about 0.254 mm, a back rake angle for the PCD element of about 20 degrees, an in-feed for the PDC of about 6.35 mm/rev, and a rotary speed of the workpiece to be cut of about 101 RPM.

The thermal stability of a PCD element may also be evaluated by measuring the distance cut in a Barre granite workpiece prior to failure, without using coolant, in a vertical turret lathe test. The distance cut is one measure of the thermal stability of the PCD element. The test parameters may be a depth of cut for the PCD element of about 1.27 mm, a back rake angle for the PCD element of about 20 degrees, an in-feed for the PCD element of about 1.524 mm/rev, and a cutting speed of the workpiece to be cut of about 1.78 msec.

A wear flat will develop in the PCD element being tested during both the abrasion resistance and thermal stability tests discussed above. The wear volume of the PCD element may be determined using, for example, the inventive methods 200 and 300 discussed above.

Figure 5:
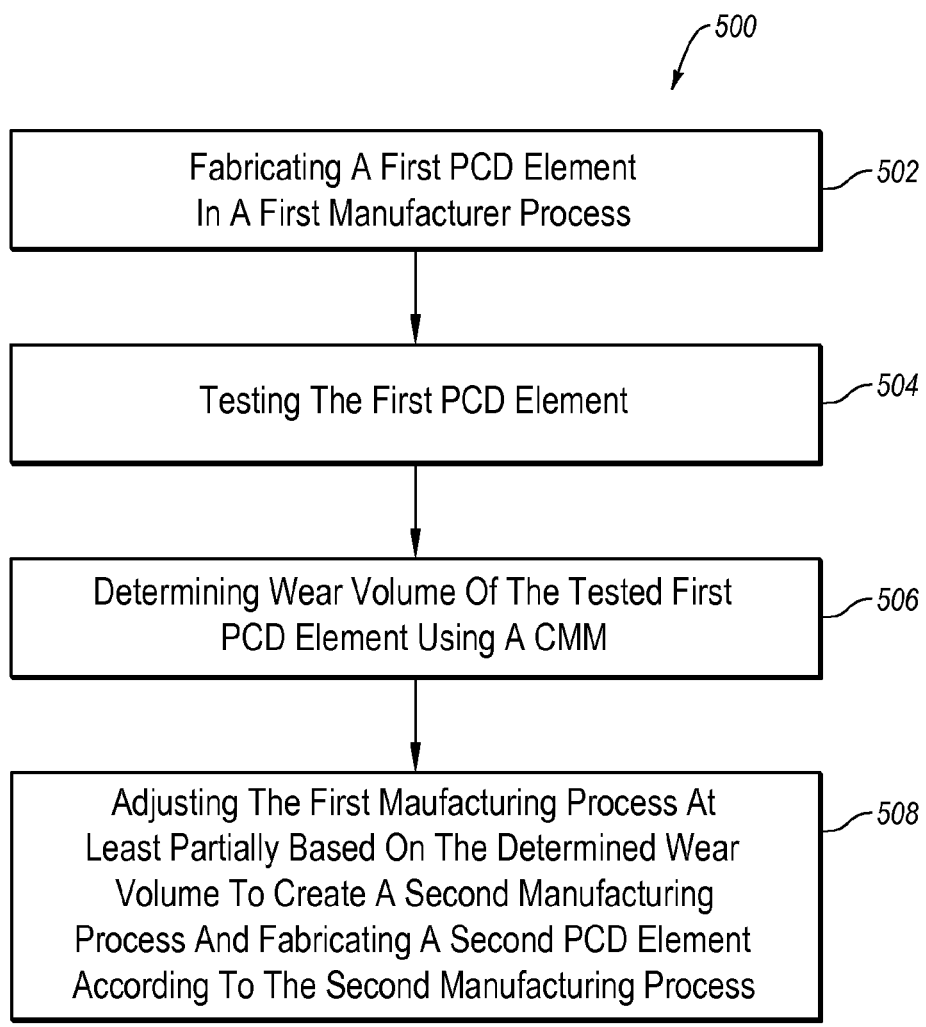
FIG. 5 is a flow chart of a method of designing a PCD element according to an embodiment.

The methods 200 and 300 may also be used when designing PCD elements. FIG. 5 is a flow chart of a method 500 of designing a PCD element according to an embodiment. The method 500 includes an act 502 of fabricating a first PCD element in a first manufacturing process, such as a first HPHT process. The method 500 further includes an act 504 of testing the first PCD element in a vertical turret lathe test until a wear volume develops. After testing the PCD element, the method 500 includes an act 506 of determining a wear volume of the tested first PCD element using a CMM as discussed above. In act 508, one or more process parameters of the first manufacturing process used to fabricate the first PCD element may be adjusted at least partially based on the determined wear volume of the first PCD element to create a second manufacturing process and a second PCD element may be fabricated according to the second manufacturing process, such as a second HPHT process.

In an embodiment, the process may be repeated one or more times. For example, the second PCD element fabricating according to the adjusted manufacturing process may be tested as in act 504, the wear volume of the PCD element may be determined using the CMM, and (if desired or needed), the second manufacturing process used to fabricate the second PCD element may be adjusted.

In an embodiment, the one or more process parameters that may be adjusted in the method 500 may affect synthesis of the diamond structure (e.g., the extent of diamond-to-diamond bonding) in the PCD element. In another embodiment, the process parameters that may be adjusted in the method 500 may affect wear resistance and/or thermal stability of the PCD element. Suitable examples of process parameters that may be adjusted at least partially based on the determined wear volume of the PCD element include, but are not limited to, HPHT sintering temperature, HPHT sintering pressure, precursor diamond particle size and/or composition used to form the PCD element, catalyst composition, amount of catalyst used in the fabrication of the PCD element, composition of a leaching medium used to leach catalyst from the PCD element, pH of an acid composition used to leach catalyst from the PCD element, leaching time used in a leaching process to leach catalyst from the PCD element, leaching temperature used to leach catalyst from the PCD element, leaching pressure used to leach catalyst from the PCD element, combinations thereof, or another suitable process parameter.

In an embodiment, the sintering temperature and/or the sintering pressure may be adjusted to affect the fabrication of the PCD element and/or affect the performance characteristics of the PCD element. As discussed in greater detail below, PCD elements are fabricated by placing diamond particles into an HPHT cell assembly and subjecting the cell assembly and the diamond particles therein to HPHT conditions (e.g., about 1100° C. to about 2200° C., or about 1200° C. to about 1450° C. and a pressure of at least about 5 GPa, 7.5 GPa to about 15 GPa, about 9 GPa to about 12 GPa, or about 10 GPa to about 12.5 GPa) for a time sufficient to sinter the diamond particles together in the presence of a metal-solvent catalyst. The pressure values employed in the HPHT processes disclosed herein refer to the pressure in a pressure transmitting medium of the HPHT cell assembly at room temperature (e.g., about 25° C.) with application of pressure using an ultra-high pressure press and not the pressure applied to the exterior of the cell assembly. The actual pressure in the pressure transmitting medium at sintering temperature may be slightly higher. The metal-solvent catalyst may be infiltrated from substrate placed adjacent the diamond particles, provided from a thin layer of metal-solvent catalyst, mixed with the diamond particles, combinations of the foregoing, or in any suitable manner. Vertical turret lathe testing of a PCD element provides a characterization technique that enables sintering parameters to be adjusted (e.g., raising/lowering the temperature and/or the pressure and/or altering the time in the pressure cell) to affect performance parameters, such as degree of diamond grain growth, extent of diamond-to-diamond bonding, and the concentration of metal-solvent catalyst incorporated into the PCD during the HPHT process.

In another embodiment, the precursor diamond particle size used to form the PCD element may be adjusted at least partially based on the determined wear volume of the tested PCD element. The diamond particles used to fabricate the PCD element may exhibit an average particle size of, for example, about 50 μm or less, such as about 30 μm or less, about 20 μm or less, about 10 μm to about 18 μm or, about 15 μm to about 18 μm. In some embodiments, the average particle size of the diamond particles may be about 10 μm or less, such as about 2 μm to about 5 μm or submicron. It is noted that the sintered diamond grain size in the PCD element may differ from the average particle size of the mass of diamond particles prior to sintering due to a variety of different physical processes, such as grain growth, diamond particle fracturing, carbon provided from another carbon source (e.g., dissolved carbon in the metal-solvent catalyst), or combinations of the foregoing.

In yet another embodiment, one or more of a catalyst composition, an amount of catalyst used in the fabrication of the PCD element, or a catalyst concentration in the fabricated-un-leached PCD element may be at least partially based on the determined wear volume of the tested PCD element. Metal-solvent catalyst concentration and/or catalyst composition may affect performance of the PCD elements by affecting, for example, thermal stability of the PCD element, impact resistance, and chemical stability.

Metal-solvent catalyst may be introduced into the PCD element by any number of processes. If, for example, the substrate includes a metal-solvent catalyst, the metal-solvent catalyst may liquefy and infiltrate the mass of precursor diamond particles during the HPHT process to promote growth between adjacent diamond particles of the mass of diamond particles to form the PCD element. For example, if the substrate is a cobalt-cemented tungsten carbide substrate, cobalt from the substrate may be liquefied and infiltrate the mass of diamond particles to catalyze formation of the PCD element. Sintering temperature and/or pressure and precursor diamond particle size may affect the amount of catalyst that infiltrates into the PCD element during the HPHT process.

Catalyst concentration in the PCD element may also be altered on subsequent to HPHT sintering by leaching at least a portion of the catalyst from the PCD element using an acid leaching process. Acid leaching is a time consuming and often difficult process. Monitoring the catalyst concentration in the PCD element before, during, and after the leaching process (e.g., by measuring magnetic saturation) may enable the leaching process parameters to be adjusted in order to achieve desired characteristics in the PCD element and/or a selected catalyst concentration in the PCD element after leaching.

In one embodiment, the concentration of catalyst in the PCD element either before or after leaching may be less than about 5 weight % ("wt %"). For example, the concentration of catalyst in the PCD element either before or after leaching is less than about 2 wt %, less than about 1 wt %, or about 0.5 wt % to about 1.5 wt %.

At least partially based on the determined wear volume of the PCD element, one or more characteristics of the acid composition used to leach catalyst from the PCD element, pH of the acid composition used to leach catalyst from the PCD element, leaching time used in a leaching process to leach catalyst from the PCD element, leaching temperature used to leach catalyst from the PCD element, leaching pressure and/or temperature used to leach catalyst from the PCD element may be adjusted, or combinations of the foregoing.

II. PCD Elements and PDCs, and Applications for PCD Elements and PDCs

Figure 6:
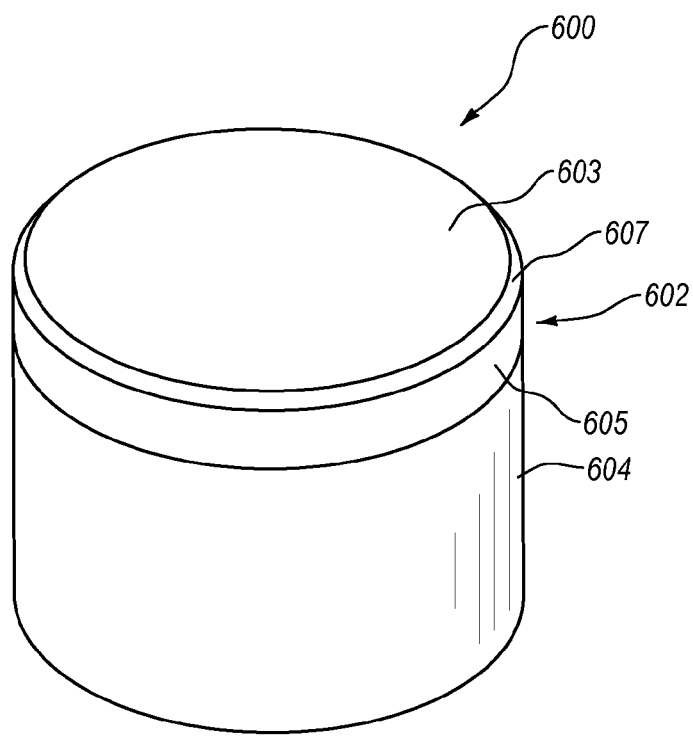
FIG. 6 is an isometric view of a PDC to be tested according to an embodiment.

PCD elements that may be tested and characterized using the methods disclosed herein include one-step and two-step PDCs including PCD tables attached to a substrate and free-standing PCD tables/elements. A one-step PDC may include a PCD table integrally formed and bonded to a cemented carbide substrate. The PCD table includes directly bonded-together diamond grains exhibiting diamond-to-diamond bonding (e.g., $sp^3$ bonding) therebetween that define a plurality of interstitial regions. FIG. 6 illustrates an embodiment of a PDC 600 including a PCD table 602 and a cemented carbide substrate 604. The PCD table 602 includes at least one lateral surface 605, an upper exterior working surface 603, and may include an optional chamfer 607 formed therebetween. It is noted that at least a portion of the at least one lateral surface 605 and/or the chamfer 607 may also function as a working surface (e.g., that contacts a subterranean formation during drilling operations).

A metal-solvent catalyst (e.g., iron, nickel, cobalt, or alloys thereof) is disposed in at least a portion of the interstitial regions between adjacent diamond grains. The cemented carbide substrate 604 may comprise tungsten carbide, tantalum carbide, vanadium carbide, niobium carbide, chromium carbide, titanium carbide, or combinations of the foregoing carbides cemented with iron, nickel, cobalt, or alloys of the foregoing metals. For example, the cemented carbide substrate may comprise cobalt-cemented tungsten carbide.

Generally, a one-step PDC may be formed by placing un-bonded diamond particles adjacent to a cemented carbide substrate and subjecting the diamond particles and the cemented carbide substrate to an HPHT process under diamond-stable HPHT conditions. During the HPHT process, metal-solvent catalyst from the cemented carbide substrate at least partially melts and sweeps into interstitial regions between the diamond particles to catalyze growth of diamond and formation of diamond-to-diamond bonding between adjacent diamond particles so that a PCD table is formed that bonds to the cemented carbide substrate upon cooling from the HPHT process.

A two-step PDC may also be formed in which an at least partially leached PCD table (i.e., a freestanding PCD table formed in an initial HPHT process as discussed in more detail below) may be placed adjacent to a cemented carbide substrate and subjected to an HPHT process under diamond-stable conditions. During the HPHT process, an infiltrant from the cemented carbide substrate or other source at least partially infiltrates into the interstitial regions of the at least partially leached PCD table and bonds the at least partially infiltrated PCD table to the cemented carbide substrate upon cooling from the HPHT process.

The at least partially leached PCD table may be formed by separating the PCD table from a one-step PDC by removing the cemented carbide substrate via any suitable process (e.g., grinding, machining, laser cutting, EDM cutting, or combinations thereof) and leaching the metal-solvent catalyst from the PCD table in a suitable acid. The at least partially leached PCD table may also be formed by other methods, such as sintering diamond particles in the presence of a metal-solvent catalyst to form a PCD table or disk and leaching the PCD table in a suitable acid.

Figure 7:
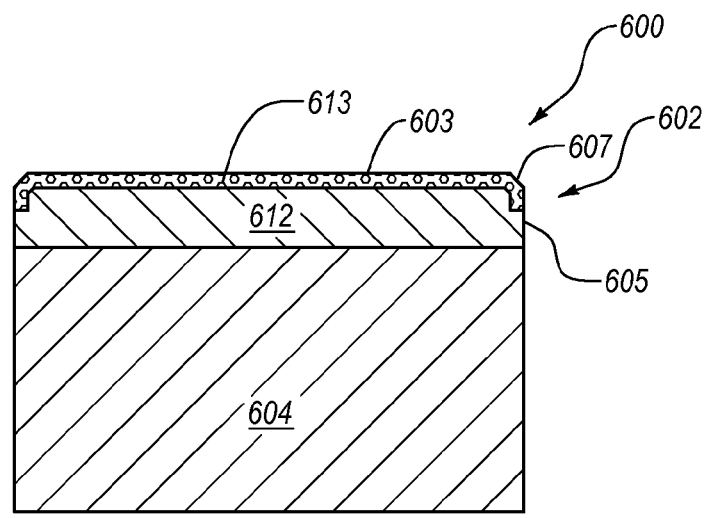
FIG. 7 is a cross-sectional view of the PDC shown in FIG. 6 including a leached region formed in the PCD table according to an embodiment.

Referring to FIG. 7, both one-step and two-step PDCs may be subjected to a leaching process to remove a portion of the metal-solvent catalyst or infiltrant from the PCD table to a selected depth and from one or more exterior surfaces to form a leached region 610, with the underlying unaffected region of the PCD table 602 labeled as 612. Removal of the metal-solvent catalyst or infiltrant may help improve thermal stability and/or wear resistance of the PCD table during use. Example acids used in leaching include, but are not limited to, aqua regia, nitric acid, hydrofluoric acid, and mixtures thereof. For example, leaching the PCD table 602 may form the leached region 610 that extends inwardly from the exterior surface 603, the lateral surface 605, and the chamfer 607 to a selected leached depth. The selected leached depth may be about 100 µm to about 1000 µm, about 100 µm to about 300 µm, about 300 µm to about 425 µm, about 350 µm to about 400 µm, about 350 µm to about 375 µm, about 375 µm to about 400 µm, about 500 µm to about 650 µm, or about 650 µm to about 800 µm.

The bonded-together diamond grains of the PCD table may exhibit an average grain size of about 100 µm or less, about 40 µm or less, such as about 30 µm or less, about 25 µm or less, or about 20 µm or less. For example, the average grain size of the diamond grains may be about 10 µm to about 18 µm, about 8 µm to about 15 µm, about 9 µm to about 12 µm, or about 15 µm to about 25 µm. In some embodiments, the average grain size of the diamond grains may be about 10 µm or less, such as about 2 µm to about 5 µm or submicron.

The diamond particle size distribution of the diamond particles that are HPHT processed may exhibit a single mode, or may be a bimodal or greater grain size distribution. In an embodiment, the diamond particles may comprise a relatively larger size and at least one relatively smaller size. As used herein, the phrases "relatively larger" and "relatively smaller" refer to particle sizes (by any suitable method) that differ by at least a factor of two (e.g., 30 µm and 15 µm). According to various embodiments, the diamond particles may include a portion exhibiting a relatively larger average particle size (e.g., 50 µm, 40 µm, 30 µm, 20 µm, 15 µm, 12 µm, 10 µm, 8 µm) and another portion exhibiting at least one relatively smaller average particle size (e.g., 6 µm, 5 µm, 4 µm, 3 µm, 2 µm, 1 µm, 0.5 µm, less than 0.5 µm, 0.1 µm, less than 0.1 µm). In an embodiment, the diamond particles may include a portion exhibiting a relatively larger average particle size between about 10 µm and about 40 µm and another portion exhibiting a relatively smaller average particle size between about 1 µm and 4 µm. In some embodiments, the diamond particles may comprise three or more different average particle sizes (e.g., one relatively larger average particle size and two or more relatively smaller average particle sizes), without limitation.

As described above, the PCD table 602 may be formed separately from or integral with the substrate 604 in an HPHT process. When formed separately, the PCD table 602 may be subsequently attached to the substrate 604 in another HPHT process (i.e., the PCD is fabricated in a two-step process). The temperature of such HPHT processes may typically be at least about 1000° C. (e.g., about 1200° C. to about 1600° C.) and the pressure of the HPHT process may typically be at least about 4.0 GPa (e.g., about 5.0 GPa to about 12.0 GPa, about 7.0 GPa to about 9.0 GPa, about 6.0 GPa to about 8.0 GPa, or about 9.0 GPa to about 12.0 GPa).

Additional details about one-step and two-step PDCs and other PCD elements that may be tested using any of the testing/characterization techniques disclosed herein can be found in U.S. Pat. No. 7,866,418; and U.S. application Ser. Nos. 12/961,787 and 11/545,929, the contents of each of the foregoing applications is incorporated herein, in their entirety, by this reference.

Figure 8:
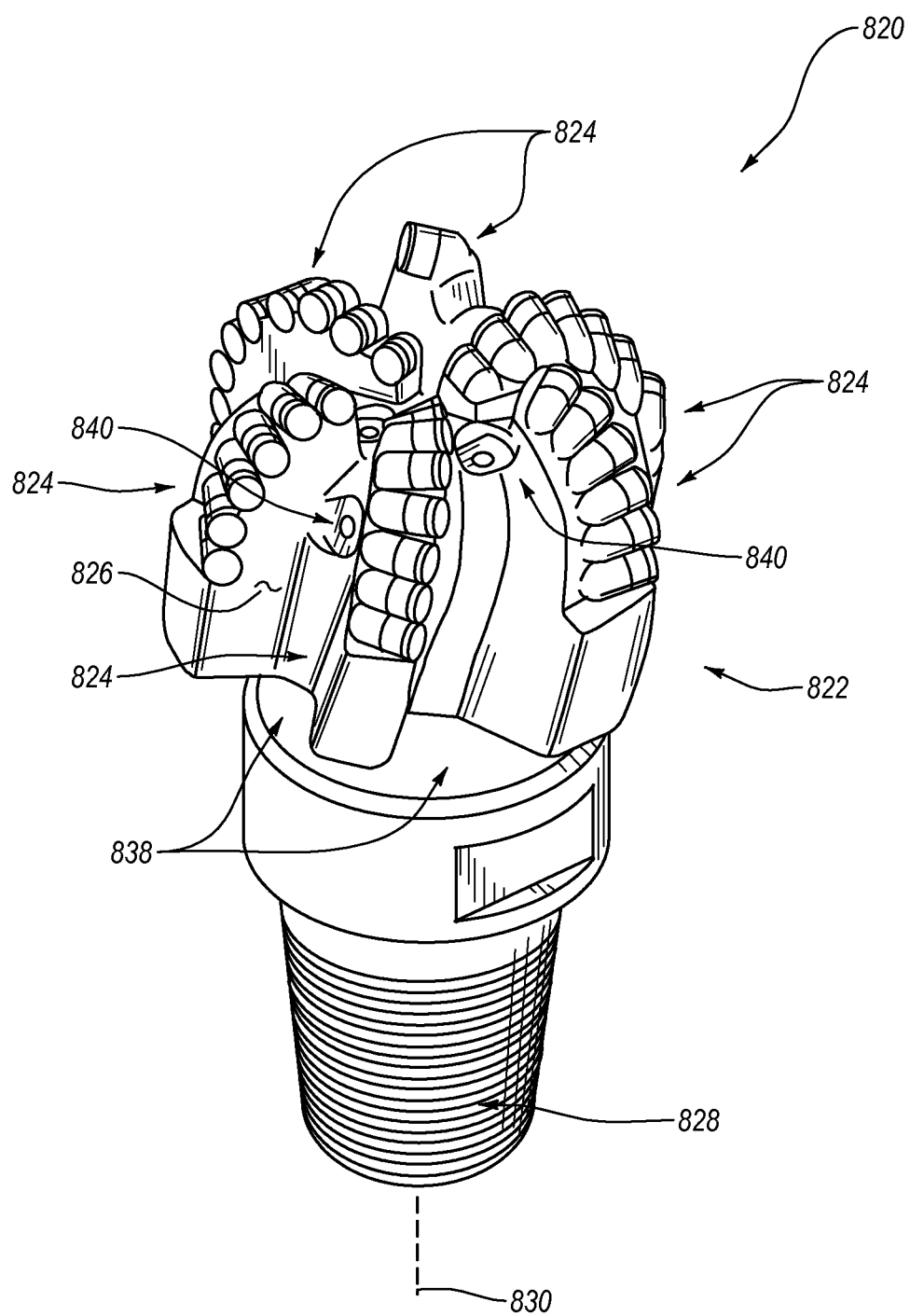
FIG. 8 is an isometric view of a rotary drill bit including PCD elements that have been tested and/or designed in accordance with an embodiment of the methods disclosed herein.
Figure 9:
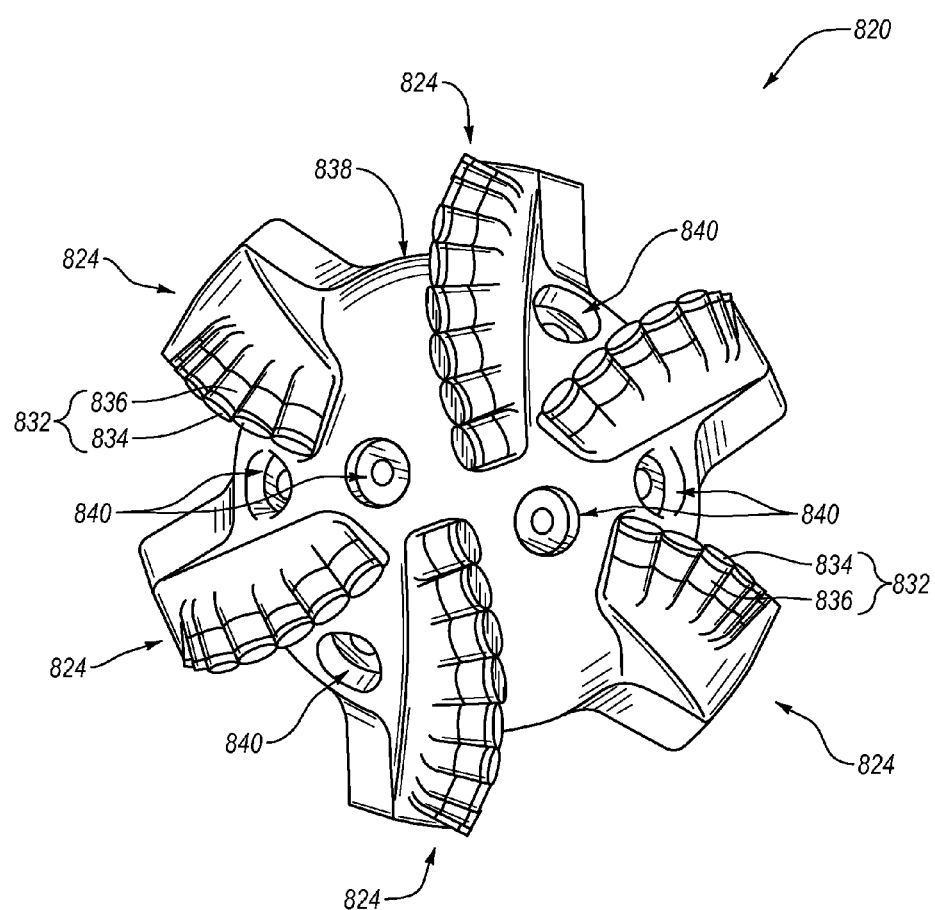
FIG. 9 is a top view of the rotary drill bit of FIG. 8.

The tested/characterized/designed PCD elements may be used in a variety of applications, such as PCD cutting elements on rotary drill bits. FIG. 8 is an isometric view and FIG. 9 is a top elevation view of an embodiment of a rotary drill bit 820. The rotary drill bit 820 includes at least one PCD element, such as a PDC, tested/characterized/designed according to any of the previously described methods. The rotary drill bit 820 comprises a bit body 822 that includes radially and longitudinally extending blades 824 with leading faces 826, and a threaded pin connection 828 for connecting the bit body 822 to a drilling string. The bit body 822 defines a leading end structure for drilling into a subterranean formation by rotation about a longitudinal axis 830 and application of weight-on-bit. At least one PCD cutting element 832, configured according to any of the previously described PCD elements (e.g., the PDC shown in FIG. 6), may be affixed to the bit body 822. With reference to FIG. 9, each of a plurality of PCD cutting elements 832 is secured to the blades 824. For example, each cutting element 832 may include a PCD table 834 bonded to a substrate 836. More generally, the cutting elements 832 may comprise any PCD or other superabrasive element disclosed herein, without limitation. Also, circumferentially adjacent blades 824 so-called junk slots 838 are defined therebetween, as known in the art. Additionally, the rotary drill bit 820 may include a plurality of nozzle cavities 840 for communicating drilling fluid from the interior of the rotary drill bit 820 to the cutting elements 832.

FIGS. 8 and 9 merely depict one embodiment of a rotary drill bit that employs at least one cutting element that comprises a superabrasive compact suitable for analysis and fabrication in accordance with the disclosed embodiments, without limitation. The rotary drill bit 820 is used to represent any number of earth-boring tools or drilling tools, including, for example, core bits, roller-cone bits, fixed-cutter bits, eccentric bits, bicenter bits, reamers, reamer wings, or any other downhole tool including superabrasive compacts, without limitation.

The tested/characterized/designed PCD elements disclosed herein may also be utilized in applications other than cutting technology. For example, the disclosed tested/characterized/designed PCD elements may be used in wire dies, bearings, artificial joints, inserts, cutting elements, and heat sinks. Thus, any of the tested/characterized/designed PCD elements disclosed herein may be employed in an article of manufacture including at least one superabrasive element or compact.

Thus, the embodiments of tested/characterized/designed PCD elements disclosed herein may be used in any apparatus or structure in which at least one conventional superabrasive compact is typically used. In one embodiment, a rotor and a stator, assembled to form a thrust-bearing apparatus, may each include one or more superabrasive compacts configured according to any of the embodiments disclosed herein and may be operably assembled to a downhole drilling assembly. U.S. Pat. Nos. 4,410,054; 4,560,014; 5,364,192; 5,368,398; and 5,480,233, the disclosure of each of which is incorporated herein, in its entirety, by this reference, disclose subterranean drilling systems within which bearing apparatuses utilizing PCD elements disclosed herein may be incorporated. The embodiments of the tested/characterized/designed PCD elements disclosed herein may also form all or part of heat sinks, wire dies, bearing elements, cutting elements, cutting inserts (e.g., on a roller-cone-type drill bit), machining inserts, or any other article of manufacture as known in the art. Other examples of articles of manufacture that may use any of the superabrasive compacts disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,180,022; 5,460,233; 5,544,713; 6,793,681; and 7,870,913, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A method for characterizing a polycrystalline diamond ("PCD") element that is tested, comprising:
    scanning an initial exterior of the PCD element with a laser;
    cutting a workpiece with the PCD element so that the PCD element develops a wear volume;
    scanning a post-cut exterior of the PCD element with the laser after cutting the workpiece; and
    determining the wear volume of the PCD element at least partially based on the post-cut exterior and the initial exterior of the PCD element.

2. The method of claim 1 wherein scanning an initial exterior of the PCD element with a laser includes scanning the initial exterior of the PCD element with a laser coordinate measuring machine, and wherein scanning a post-cut exterior of the PCD element with the laser includes scanning the post-cut exterior of the PCD element with the laser coordinate measuring machine.

3. The method of claim 1, further comprising:
    measuring the initial exterior including generating a first computer model from data generated from scanning the initial exterior; and
    measuring the post-cut exterior including generating a second computer model from data generated from scanning the post-cut exterior.

4. The method of claim 3 wherein measuring the post-cut exterior includes measuring the post-cut exterior of the PCD element at different stages during the cutting of the workpiece.

5. The method of claim 4, further comprising determining a $G_{ratio}$ for the PCD element based at least partially on the respective post-cut exteriors measured at the different stages.

6. The method of claim 3 wherein measuring the post-cut exterior includes measuring the post-cut exterior using a laser coordinate measuring machine.

7. The method of claim 6 wherein measuring the post-cut exterior using a laser coordinate measuring machine includes scanning the PCD element with the laser coordinate measuring machine.

8. The method of claim 1 wherein cutting a workpiece with the PCD element so that the PCD element develops a wear volume includes cutting the workpiece with the PCD element in a vertical turret lathe.

9. The method of claim 1 wherein determining the wear volume of the PCD element at least partially based on the post-cut exterior and the initial exterior of the PCD element includes calculating a difference between the initial exterior and the post-cut exterior of the PCD element.

10. The method of claim 1 wherein the PCD element includes a polycrystalline diamond compact.

11. The method of claim 10 wherein the polycrystalline diamond compact includes a PCD table bonded to a substrate.

12. The method of claim 1 wherein the PCD element includes a freestanding polycrystalline diamond element without a substrate.

13. A method for designing a manufacturing process for a polycrystalline diamond ("PCD") element, the method comprising:
    measuring an initial exterior of a first PCD element using a laser coordinate measuring machine, wherein the first PCD element was fabricated in a first manufacturing process;
    cutting a workpiece with the first PCD element so that the first PCD element develops a wear volume;
    measuring a post-cut exterior of the first PCD element after cutting the workpiece using the laser coordinate measuring machine;
    determining the wear volume of the first PCD element at least partially based on the post-cut exterior and the initial exterior of the first PCD element; and
    modifying the manufacturing process used to fabricate the first PCD element at least partially based on the wear volume.

14. The method of claim 13 wherein the first PCD element includes a polycrystalline diamond compact.

15. The method of claim 14 wherein the polycrystalline diamond compact includes a PCD table bonded to a substrate.

16. The method of claim 15 wherein the first PCD element includes a freestanding polycrystalline diamond element without a substrate.

17. A method for characterizing a polycrystalline diamond compact that is tested, comprising:
    scanning an initial exterior of the polycrystalline diamond compact with a scanning light device;

responsive to scanning the initial exterior, generating a first computer model of the initial exterior;

cutting a workpiece with the polycrystalline diamond compact so that the polycrystalline diamond compact develops a wear volume;

scanning a post-cut exterior of the polycrystalline diamond compact after cutting the workpiece with the scanning light device;

responsive to scanning the post-cut exterior, generating a second computer model of the post-cut exterior; and determining the wear volume of the polycrystalline diamond compact at least partially based on the second computer model of the post-cut exterior and the first computer model of the initial exterior of the polycrystalline diamond compact.

18. The method of claim 17 wherein the scanning light device includes a laser.

19. The method of claim 17 wherein the scanning light device includes a laser coordinate measuring machine.

20. The method of claim 17, further comprising:
measuring the initial exterior from the first computer model; and
measuring the post-cut exterior from the second computer model.

21. The method of claim 17 wherein cutting a workpiece with the polycrystalline diamond compact so that the polycrystalline diamond compact develops a wear volume includes cutting the workpiece with the polycrystalline diamond compact in a vertical turret lathe.

22. The method of claim 17 wherein the polycrystalline diamond compact includes a PCD table bonded to a substrate.

23. The method of claim 1 wherein the polycrystalline diamond compact includes a freestanding polycrystalline diamond element without a substrate.

24. A method for characterizing a polycrystalline diamond ("PCD") element that is tested, comprising:
scanning an initial exterior of the PCD element with light;
cutting a workpiece with the PCD element so that the PCD element develops a wear volume;
scanning a post-cut exterior of the PCD element with the light after cutting the workpiece; and
determining the wear volume of the PCD element at least partially based on the post-cut exterior and the initial exterior of the PCD element.

25. The method of claim 24 wherein the light is generated with a laser.

26. The method of claim 24 wherein cutting a workpiece with the PCD element so that the PCD element develops a wear volume includes cutting the workpiece with the PCD element in a vertical turret lathe.

27. The method of claim 24 wherein the PCD element is bonded to a substrate.

28. The method of claim 1 wherein the PCD element is a freestanding polycrystalline diamond element without a substrate.

* * * * *